United States Patent [19]
Vogler et al.

[11] Patent Number: 5,326,535
[45] Date of Patent: Jul. 5, 1994

[54] TUBE HAVING UNITARY BLOOD COAGULATION ACTIVATOR AND METHOD FOR ITS PREPARATION

[75] Inventors: Erwin A. Vogler, Newhill; Jane C. Graper, Durham; Garry R. Harper, Raleigh, all of N.C.

[73] Assignee: Becton, Dickinson and Company, Franklin Lakes, N.J.

[21] Appl. No.: 54,340

[22] Filed: Apr. 30, 1993

[51] Int. Cl.⁵ .............................................. B01L 3/00
[52] U.S. Cl. .................................. 422/102; 422/73; 604/403; 604/415; 436/69
[58] Field of Search ............... 427/2, 230, 307; 604/403, 415; 422/73, 102, 99; 436/69

[56] References Cited

U.S. PATENT DOCUMENTS

| | | | |
|---|---|---|---|
| 4,153,739 | 5/1979 | Kessler | 427/2 |
| 4,257,886 | 3/1981 | Kessler | 210/516 |
| 4,420,517 | 12/1983 | Ali | 422/73 |
| 4,579,828 | 4/1986 | Ali | 422/73 |
| 4,887,396 | 12/1989 | Lukianoff | 51/391 |
| 5,213,765 | 5/1993 | Kasai et al. | 422/102 |

OTHER PUBLICATIONS

"Baxter Evacuated Clot Activator Tubes" p. 154 1991.

*Primary Examiner*—James C. Housel
*Assistant Examiner*—Lien Tran
*Attorney, Agent, or Firm*—Richard E. Brown

[57] ABSTRACT

A blood collection container is coated on its inside wall with a unitarily immobilized clotting activator. The activator may be applied to the surface by an adhesive or by rendering the inside wall surface sticky with a solvent and partially absorbing the activator into the sticky surface.

8 Claims, 3 Drawing Sheets

TUBE HAVING UNITARY BLOOD COAGULATION ACTIVATOR AND METHOD FOR ITS PREPARATION

BACKGROUND OF THE INVENTION

1. Field of the Invention

This invention relates to blood collection and, more particularly, relates to a blood sample collection tube and a method for its preparation.

2. Background

Blood samples are routinely taken in evacuated tubes, such as glass VACUTAINER TM tubes (Becton, Dickinson and Company). One end of a double-ended needle is inserted into a patient's vein. The other end of the needle then punctures a septum covering the open end of the VACUTAINER TM tube so that the vacuum in the tube draws the blood sample through the needle into the tube. Using this technique, a plurality of samples can be taken using a single needle puncture of the skin. Plastic tubes have also been proposed for blood collection. Plastic offers a number of advantages such as to lower breakage than glass tubes, less weight in shipment, and easier disposal by incineration. Blood collected in evacuated tubes often must be clotted prior to clinical examination. It is desirable to form a dense clot as rapidly and completely as possible to facilitate clean separation of the clot from the serum layer by centrifugation. To achieve this end, both plastic and glass blood collection tubes frequently employ a clot activator. Typical activators are diatomaceous earth and particles of inorganic silicates, or biochemicals such as ellagic acid and thromboplastin. In one line of commercial blood collection tubes, for example, a coating of silicate particles in polyvinylpyrrolidone (PVP, a water soluble polymer) is affixed to the inside of the tube. When blood enters the tube, the PVP dissolves and silicate particles are released to initiate clotting. The PVP enters both the serum and clot.

A problem with particulate activators is that finely divided particles may not pellet completely with the clot and may thus contaminate the serum layer and interfere with certain blood analyses. In addition, particles suspended in the serum may foul automatic blood analysis instruments. For highly specialized applications, such as blood banking, it is unacceptable to have particulates in the cell mass of a blood clot because these cells are used in blood typing analyses. On the other hand, soluble biochemical activators can be disadvantageous because these cannot be easily separated from either serum or blood clot and can interfere with both chemical and hematological assays.

There is need in the art of blood collection for a blood clot activator that enhances the rate of blood coagulation but which does not remain in the serum layer or become part of the clot on centrifugation, thus avoiding potential interference with clinical tests.

SUMMARY OF THE INVENTION

A blood collection tube has a bottom wall continuous with a side wall. The side wall defines an open end and the bottom wall defines a closed end. Together the bottom and side walls define an inside wall surface. The open end preferably is covered by a puncturable septum.

The inside wall surface is unitarily coated with a multiplicity of particles of a blood clotting activator. In this disclosure, the term unitary means that the particles are permanently affixed to the inside wall surface so as to be impervious to removal during routine blood sample collection, centrifugation and transportation.

Preferred tubes are plastic, such as polystyrene, and preferred particles are inorganic silicates.

A second aspect of the invention is a method to make the tube of the invention. In one embodiment of the method, the inside wall of the tube is treated with a solvent to soften the plastic. The softened and sticky inside wall is then contacted with a powder of the activator so that particles of the activator are partially absorbed into and unitarily affixed to the plastic. In a second method embodiment, the inside wall surface is coated with an adhesive and the powdered activator is affixed thereto.

Thus, the invention provides a plastic tube which retains the advantages of plastic and overcomes the disadvantage of poor and slow coagulation in plastic. The particles of clotting activator of the tube are unitarily affixed to the inside wall of the tube, with a portion of the particles exposed to a blood sample, so that clotting is activated but the particles remain affixed to the tube and do not contaminate either the serum or the clot. In addition, no soluble materials such as binders or biological activators are present to contaminate the serum sample or clot.

DETAILED DESCRIPTION

While this invention is satisfied by embodiments in many different forms, there will herein be described in detail preferred embodiments of the invention with the understanding that the present disclosure is to be considered as exemplary of the principles of the invention and is not intended to limit the invention to the embodiments illustrated and described. The scope of the invention will be measured by the appended claims and their equivalents.

The blood collection container of the invention may be any container having continuous bottom and side walls defining a closed end and open end respectively. The bottom wall and the side wall together define an inside wall surface. Suitable containers are, for example bottles, vials, flasks and the like, preferably tubes. The invention will henceforth be described in terms of the preferred tube.

Figure 1:
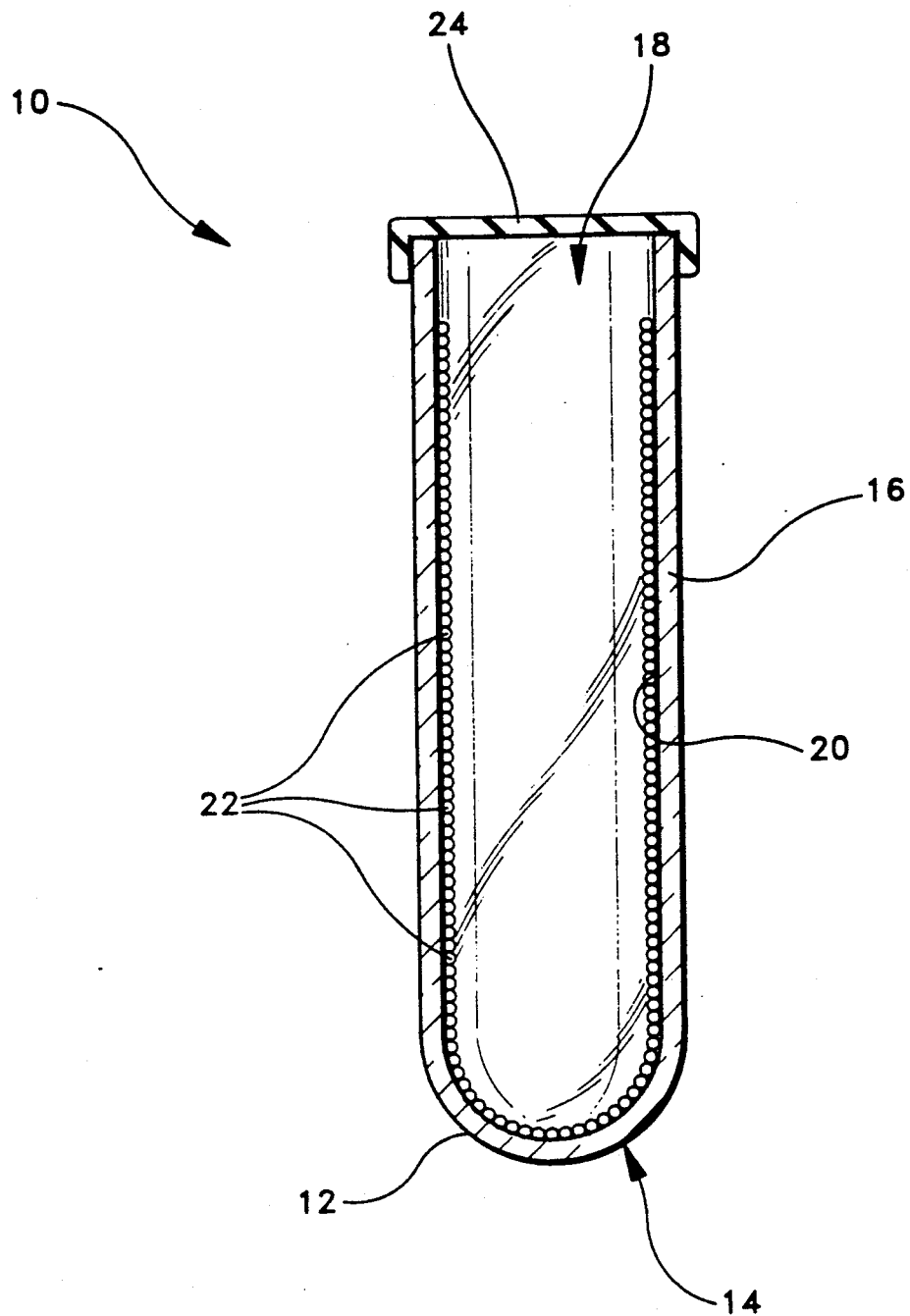
FIG. 1 is a perspective view of the blood collection tube of the invention.

The tube may preferably be combined with a puncturable septum over the open end and may be evacuated. Evacuated tubes for blood collection are standard in the art as, for example, VACUTAINER TM brand tubes (Becton, Dickinson and Company). FIG. 1 illustrates the tube of the invention. A tube 10 has a bottom wall 12 defining a closed end 14 and a side wall 16 defining an open end 18. Bottom wall 12 and side wall 14 are continuous and together define an inside wall surface 20. A multiplicity of activating particles 22 are unitarily affixed to inside wall surface 20. The open end 18 of tube 10 is covered with puncturable septum 24.

The tube may be of glass or preferably plastic. Suitable plastics are polyvinyl chloride, polypropylene (PP), polyethylene terephthalate (PET) and preferably polystyrene (PS).

Particles of a blood coagulation activator are unitarily affixed to all or a portion of the inside wall of the tube. The portion of the tube surface to be coated depends on the desired speed of coagulation and the density of coating particles, and may be about 1-100% of the inside wall surface, preferably about 40-80%.

Suitable activators are particles of titanium dioxide, cellulose, ceramic materials such as earthenware, porcelain, brick and the like. Preferred activators are siliceous materials such as glass, sand and diatomaceous earth. The most preferred activator is a particle of silicate, such as sodium, potassium, aluminum and magnesium silicate.

The activating particles of the invention may be of any shape but preferably may be approximately spherical. The particles may be about 0.01 to 100, preferably about 0.1 to 20 microns in the largest cross-sectional dimension.

The particle may be unitarily affixed to the inside wall surface of the tube by any means which leaves a portion of the particle exposed to a blood sample to be taken in the tube. Thus a thin coating of any adhesive which is blood compatible and which is not dissolved by blood may be applied to the inside wall surface of the tube. The adhesive may be applied by spraying, brushing or solvent solution deposition, after which the solvent is removed by any convenient method.

Suitable adhesives are, for example, any of the commercially available pressure sensitive acrylic, polyurethane or other polymeric adhesives which are impervious to blood. The coating of adhesive may be about 0.01 to 10, preferably about 0.1 to 1 millimeters thick.

Application of the particles to the adhesive coated surface may be done by any means which results in a substantially uniform deposition of the particles. Preferably the particles are simply dusted onto the adhesive layer so that they are substantially one particle deep and noncontinuous but almost in contact with each other. Advantageously the tubes may be rotated or tumbled during contact with the dust of particles to aid in uniform application. In this way, the maximum exposed surface area of particles is obtained.

The adhesive may then be allowed to dry or cure completely, and particles which are not unitarily affixed may be removed by any convenient procedure, such as rinsing with water or exposure to an air jet.

Alternatively, the article of the invention may be made by melt processing the polymer containing the particles so that the article contains the particles throughout. Any melt processing as known in the art, such as molding and extrusion, may be used. Subsequently, the outside layer of plastic may be partially removed so that the particles, while still unitarily adhered to the article, are partially exposed. For example, sufficient polymers may be removed to expose the particles by treatment with a solvent or by chemical or plasma oxidation of the outside layer of polymer.

In the preferred method for applying the particles which is particularly advantageous for plastic tubes, the tubes are first brought into contact for about 1 to 60 seconds with a solvent which partially dissolves the plastic on the inside wall. This process softens the outer layer of plastic and makes the surface rough and sticky. After solvent treatment the solvent may be removed by any suitable method, such as decantation or evaporation, and, while the plastic surface is sticky, the particle may be dusted onto the sticky surface. The particles adhere to and become partially embedded in the sticky polymer and are thus unitarily affixed. Removal of particles which are not securely affixed may be performed as described above.

Suitable solvents for this embodiment of the invention may be acetonitrile, tetrahydrofuran, ethyl acetate and the like. A particularly useful solvent is acetone.

The effectiveness of the activating particles may be determined by the time required for clotting as compared to clotting time for the untreated surface.

The following examples are provided to further describe the invention but are not to be considered as limitative of the invention.

EXAMPLE I

Figure 2:
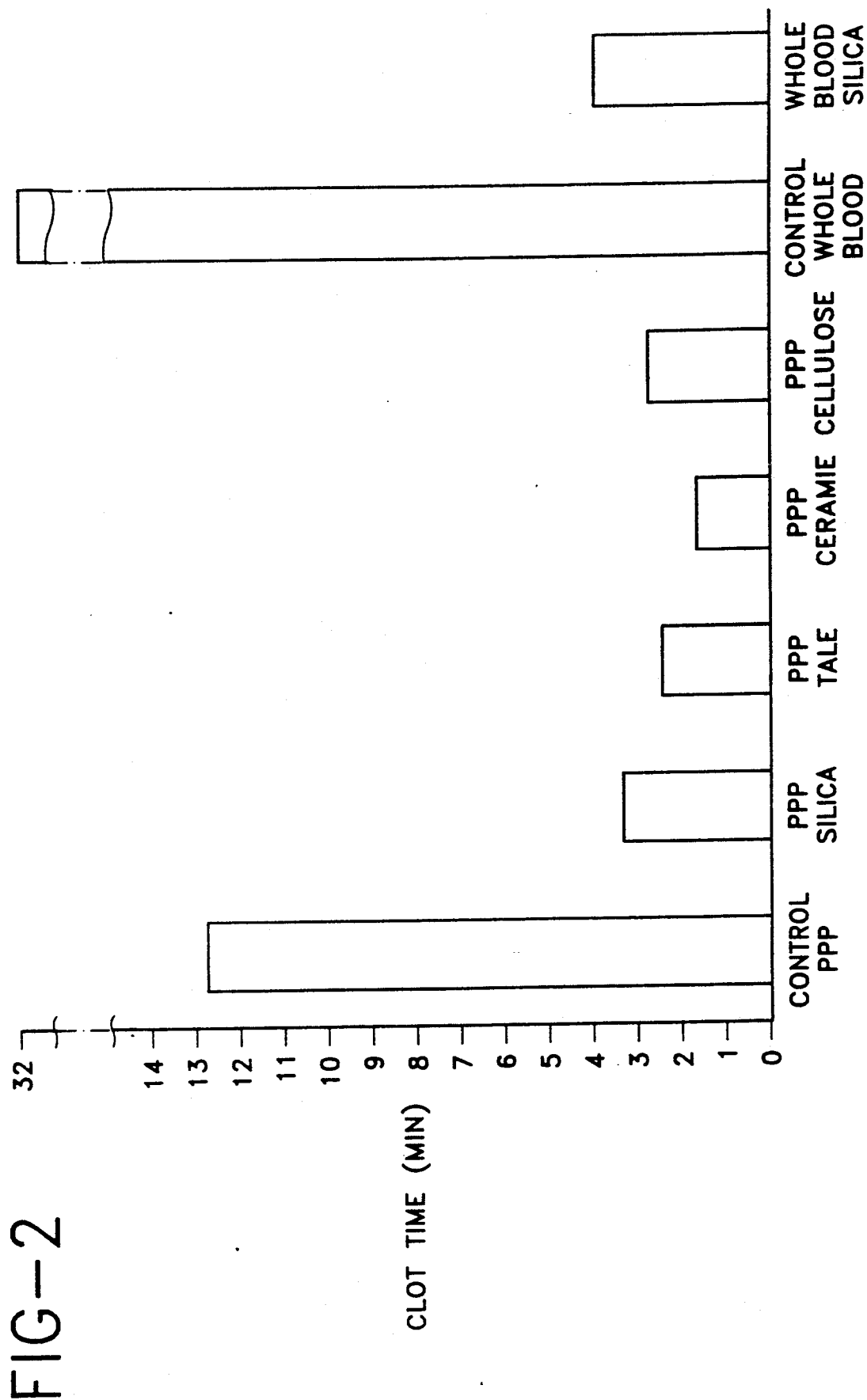
FIGS. 2 and 3 compare the rate of blood clotting in representative tubes of the invention with control tubes.

A PS tube (10×75 mm) was filled about halfway with acetone and set aside at room temperature for 15 seconds. The acetone was decanted and powdered silica (MINUCIL ™, Pittsburgh Sand and Glass Co.) having an average particle surface area of 5.6 $m^2/gm$ was added to the tube. The tube was rotated so that an even coating of the powder was formed over the tacky inside wall, then set aside for 10 min. to allow residual acetone to evaporate. Partially adhered powder was loosened by tapping the tube and removed by rinsing with water. After air drying, the tube was tested for clot activation by the procedure of Example III. The results of this experiment are shown in FIG. 2.

EXAMPLE II

In this same way as described in Example I, PS tubes were coated with 20 micron cellulose powder, talc (powdered magnesium silicate, 9 microns) and powdered alumina-silicate ceramic (10 micron). Clot times were determined as in Example III and are shown in FIG. 2.

EXAMPLE III

Determination of Clotting Time

Clot activating properties of the tubes prepared according to Examples I, II and IV were assessed by comparison of the time required to clot platelet poor plasma (PPP) or whole porcine (pig) blood to that in untreated PS and glass tubes. PPP was prepared by separating cells, by centrifugation, from citrated porcine blood (Environmental Diagnostics Inc.). Approximately 3 ml of PPP or whole blood were added to the tubes and equilabrated to room temperature in a water bath for 15 minutes. Following equilibration, 200 $\mu l$ of 0.2M $CaCl_2$ per ml of PPP or blood was added to initiate coagulation. Tube contents were mixed on a laboratory inverting mixer and time of clotting noted for each tube type. Clotted PPP was distinguished from non-clotted PPP by an obvious change from a fluid state to a gelatinous state which did not flow in the tube upon rotation. Clotting time was measured at this point.

EXAMPLE IV

The lower halves of PP and PET tubes (10×75 mm) were sprayed with a commercial pressure sensitive adhesive (Illinois Bronze Paint Co., Lake Zurich, Ill.). While the adhesive was still tacky, the MINUCIL ™ powder of Example I was added, and the tubes shaken to cause the powder to adhere to the adhesive. The tubes were set aside until the adhesive was fully cured and loose powder was removed as in Example I. Clot times were determined as in Example III using PPP and are given in FIG. 3.

Figure 3:
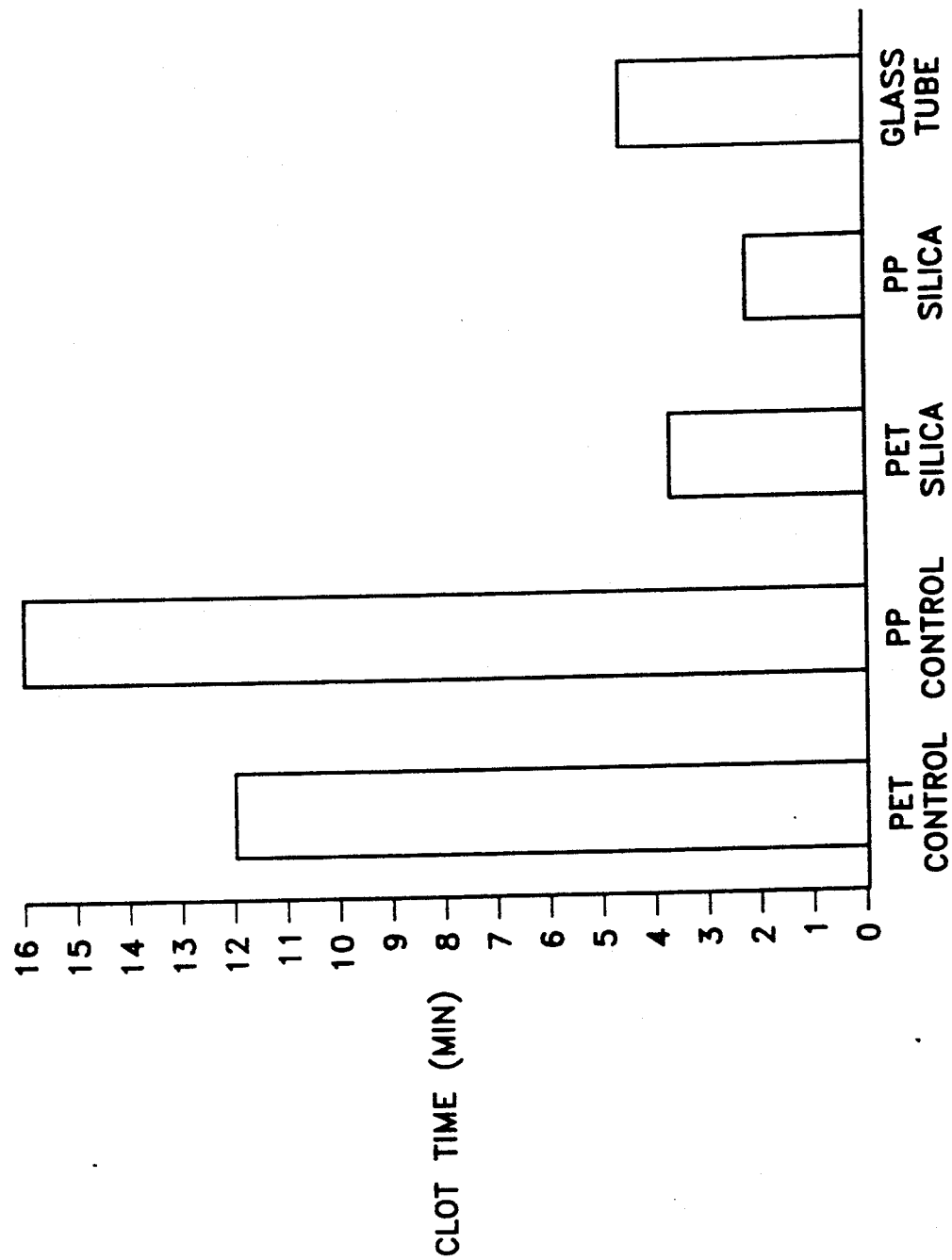

It is seen from FIGS. 2 and 3 that a unitary coating of particles of particular clotting activators on the inside wall surface of various plastic tubes reduces clotting times by factors of 4 fold or better.

What is claimed is:

1. A blood collection assembly comprising:
   a) a plastic container having a bottom wall providing a closed end and a side wall defining an open end, said side wall and bottom wall together defining an inside wall surface, at least a portion of said inside wall surface having unitarily affixed thereto particles of a blood clotting activator; and
   b) a puncturable septum over said open end, said particles being partially embedded in the plastic inside wall surface.

2. The assembly of claim 1 wherein said particle is selected from the group consisting of titanium dioxide, a metal silicate, ceramic material and siliceous material.

3. The assembly of claim 1 wherein said container is a tube.

4. The assembly of claim 1 further comprising an adhesive between said inside wall surface and said particle.

5. A method for preparing a plastic blood collection assembly comprising the steps of:
   a) contacting an inside wall surface of a plastic tube having an open end and a closed end with a solvent which causes said inside wall surface to become sticky;
   b) unitarily adhering particles of a blood clotting activator to the sticky inside wall surface, said particles being partially embedded in the plastic inside wall surface;
   c) evaporating the solvent on said inside wall surface and on said particles; and
   d) covering said open end with a puncturable septum.

6. The method of claim 5 further comprising removing particles from said inside wall surface which are not unitarily adhered to said inside wall surface.

7. A blood collection assembly produced by a process including the steps of:
   a) contacting an inside wall surface of a plastic tube having an open end and a closed end with a solvent which causes said inside wall surface to become sticky;
   b) unitarily adhering particles of a blood clotting activator to the sticky inside wall surface, said particles being partially embedded in the plastic inside wall surface;
   c) evaporating the solvent on said inside wall surface and on said particles; and
   d) covering said open end with a puncturable septum.

8. The assembly of claim 7 wherein said process further includes the step of removing particles which are not unitarily adhered to said inside wall surface.

* * * * *